US006299310B1

United States Patent
Reis

(10) Patent No.: US 6,299,310 B1
(45) Date of Patent: Oct. 9, 2001

(54) LUMINOUS INTENSITY DETECTION AND CONTROL SYSTEM FOR SLIT LAMPS AND SLIT LAMP PROJECTIONS

(75) Inventor: Werner Reis, Munich (DE)

(73) Assignee: G. Rodenstock Instrumente GmbH (DE)

( * ) Notice: Subject to any disclaimer, the term of this patent is extended or adjusted under 35 U.S.C. 154(b) by 0 days.

(21) Appl. No.: 09/725,427

(22) Filed: Nov. 29, 2000

Related U.S. Application Data

(63) Continuation of application No. PCT/DE00/00954, filed on Mar. 30, 2000.

(51) Int. Cl.⁷ ..................................................... A61B 3/10
(52) U.S. Cl. ............................................................ 351/214
(58) Field of Search .................................... 351/213, 214, 351/215, 221; 606/4, 5, 10; 600/318

(56) References Cited

U.S. PATENT DOCUMENTS 5,098,426 3/1992 Sklar et al. ............................... 606/5

Primary Examiner—George Manuel
(74) Attorney, Agent, or Firm—St. Onge Steward Johnston & Reens LLC

(57) ABSTRACT

The invention is characterised by the provision that in a slit lamp or a slit lamp projector an oblique thin glass flat with a partial reflection of the light is disposed at a defined angle relative to the optical path above the filter assembly between the latter and the "slit projector" lens (4), and in the configuration with an achromatic doublet lens between the lens assemblies in the parallel optical path, in such a way that as a result one part of the incident rays is incident as deflected light cone on a detector assembly which is arranged laterally in the housing at an angle dependent on the angle of the thin glass flat in the housing, which detector assembly measures the respectively existing luminous intensity, transmits the detected values to an evaluation and control means which compares the values so received against a predetermined maximum value, calculates the irradiation dose for the phakic or aphakic eye and, when the value is exceeded, signals this situation on an indicating alarm means and/or reduces the luminous intensity automatically to the predetermined maximum value in a controlled manner.

2 Claims, 3 Drawing Sheets

Figure 1:
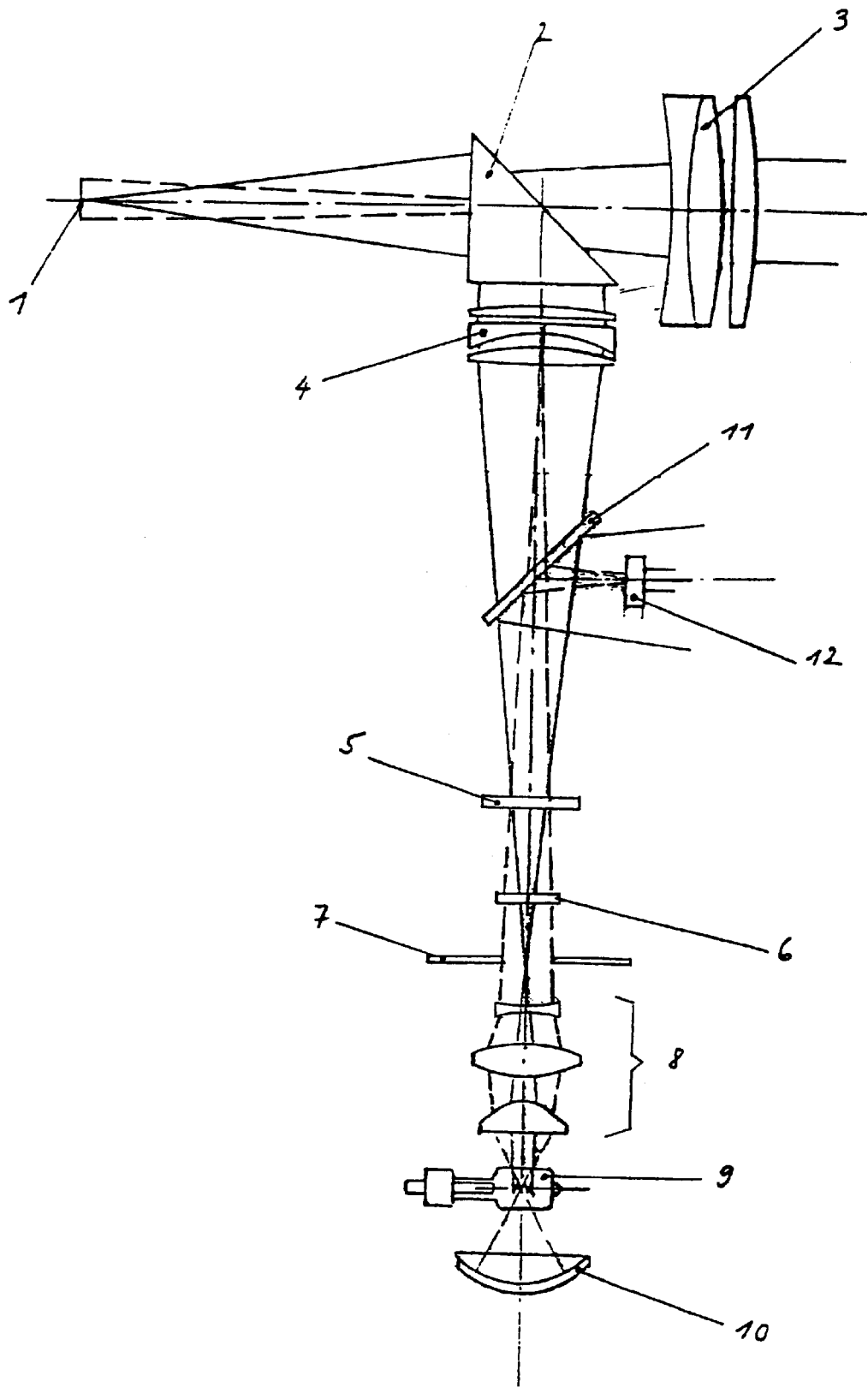

LUMINOUS INTENSITY DETECTION AND CONTROL SYSTEM FOR SLIT LAMPS AND SLIT LAMP PROJECTIONS

This is a continuation of pending International Application PCT/DE00/00954 filed on Mar. 30, 2000, which designates the United States.

FIELD OF THE INVENTION

The present invention relates to a luminous intensity detection and control system for slit lamps and slit lamp projectors.

PRIOR ART

Slit lamps or slit lamp projectors have become known which consist of a microscope and a pivotable illuminating system, which generates a slit image. They serve the purpose of an enlarged observation of the eye and its environment. Inter alia such solutions have become known in which the optical system of the slit image projector is, so to speak, an improvement of the slit image projects so far common. There the attempt was made for the first time to merge the optical condenser system with the optical lens system so as to form a highly efficient unit. The condenser serves the purpose of projecting the image of the bulb filament onto the lens or the exit prism, respectively. It is the function of the lens of the lamp to project the slit and iris diaphragm into the axis of rotation of the device, i.e. onto the eye. Furthermore, these devices comprise the following components: the lens with reflecting prism for projecting the slit and iris diaphragm, a variable aperture stop, certain variable filter systems, compensating glass flat as well as the body and the mechanical adjusting system.

The objective of the developments of slit lamps has so far been characterised by the achievement of the following properties in application:

excellent imaging quality, accommodation-free observation, several magnifying stages, slit lengths suitable for optical change-over, series-produced eyepieces for spectacle wearers, excellent slit images on account of carefully matched aperture and light conditions, high illuminating intensity and constant luminance, survey viewing at diffuse illumination with a ground or frosted glass adapted to be pivoted in front of the system, pin-sharp slit images from the front surface of the cornea up to the rear surface of the lens due to an exchangeable prism head with a variable aperture.

From the German Patent DE 195 39 371 A1 an imaging optical device is known which serves the purpose of providing a novel enlarging or reducing optical device displaying improved characteristics, which, even in observation through turbid media, creates an image of the object which is as contrasty and non-glaring as possible so that-individual details will become visible. The luminous intensity of the device and the resolution achieved with the device are very high. A device for preventing the eye under examination and to be exposed to an excessively high load by an excessive light radiation and for signalling such a condition is not envisaged.

From the German Patent DE 42 27 942 C2 a slit lamp illuminating device is known which serves to project a slit diaphragm into a target plane and which comprises the following constituents:

a light source, preferably with a high intensity, which a fibre-optical light conductor disposed downstream, a slit diaphragm downstream of the exit surface of the light conductor at a small spacing therefrom, without optical elements connected therebetween, an imaging means connected downstream of the slit diaphragm and comprising at least two optical systems producing each a converging optical effect, whereof the first one is so dimensioned that an image of the exit surface of the light conductor is created in a plane located between the target plane and the principal plane of the optical system next to the image, and wherein a collimation of the optical path for slit diaphragm imaging takes place simultaneously with the first optical system, whilst the second optical system causes the collimated optical path for slit diaphragm imaging to be focussed into the target plane, which results in a complete exploitation of the numerical aperture of the fibre-optical light conductor by the imaging means.

A means for avoiding overload with the illuminating light and for signalling this condition is not envisaged here either.

The European standard DIN EN ISO 10939 regulates, inter alia, the demands on slit lamps and slit lamp projectors. In Section 4 of that standard specifies the requirements and Section 4.4 defines particularly the demands in terms of a hazard created by optical radiation in slit lamps. There threshold levels are defined and in Section 4.4.4 the following requirement is determined specifically: "The manufacturer must provide the user with a graph which shows the relative spectral radiation intensity emitted by the slit lamp in the range from 305 nm to 1,100 nm for the case that the instrument will be operated at maximum luminous intensity and at a maximum aperture value. The emitted spectral radiation intensity must be specified for the cone of light rays after the latter's exit from the instrument.

The manufacturer is bound to specify to the user the values of the spectrally weighted photo-chemical radiant intensity and of the source of radiation for both the phakic eye $L_B$ and the aphakic eye $L_A$. These values must be determined in the cone of light rays leaving the instrument in the event that the instrument is operated at maximum luminous intensity and maximum aperture."

Pursuant to this DIN standard the manufacturer is moreover required to hand out to the user accompanying documents such as directions for use which must comply also with the requirements pursuant to Section 4.4.4 of DIN EN ISO 10939, inter alia. In practical operation it is now common practice to attach appropriate diagrams which reflect, for instance, the radiation intensity versus the applied voltage. In such an approach short-term overstrain on the eye to be examined cannot be precluded. The simplest solution were a general reduction of the illuminating intensity of the slit lamps, however with the high luminous intensity of the slit projector being the main argument in particular in the application of the slit lamps.

Even though the presently applied methods and means for determining and influencing the luminous intensity on slit lamps and slit lamp projectors satisfy the requirements specified in the DIN standard, for instance, a short-term overstraining of the eye under examination as a result of an excessively high light load cannot be precluded.

The present invention is therefore based on the problem of developing a solution which permits, on the one hand, the work on the eye under examination with a high illumination level, whilst, on the other hand, damage to the patient's eye under examination with application of the slit lamp is prevented, without a general reduction of the maximum level of the luminous intensity of the slit lamp.

BRIEF DESCRIPTION OF THE INVENTION

In accordance with the present invention this problem is solved by a luminous intensity detection and control system for slit lamps and slit lamp projectors in such a way that in a slit lamp or a slit lamp microscope an oblique thin glass flat with partial reflection of the light at a defined angle relative to the optical path of the illuminating beam is disposed above the filter assembly between the latter and the non-split objective lens slit projector in a way that one part of the beams incident thereon is incident as deflected cone of light rays on a detector or a detector assembly, respectively, which measures the respectively available luminous intensity, transmits the detected values to an evaluation and control means which compares these values so received against a predetermined maximum value, calculates the irradiation dose for the phakic eye or the aphakic eye and, when the value is exceeded, signals this condition on an indicating alarm means known per se and/or reduces the luminous intensity back to the predetermined maximum value in a controlled manner. The location of the glass flat is so important for the reason that the optical path does not vary the size of the filament image of the halogen lamp but merely amplifies or weakens it. When hence the slit illumination is, for instance, varied in terms of the width or height of the slit this variation produces an effect on the detector only in terms of a variation of the brightness. The image of the slit lamp filament is retained in unmodified form in terms of its size or position. At this location the path of the beams presents a rectangular distribution of the light so that an accommodation of the laterally disposed detector does not create any problems. The combination of the detector assembly with the brightness control of the slit projector is particularly expedient because the filter absorption is taken into consideration due to the selected site. The IR and UV fractions, which are not of interest for the application, could be masked out by means of appropriate glass types or filters.

In another embodiment the luminous intensity detection and control system for slit lamps and slit lamp projectors for devices with achromatic doublet lens (split objectives) and hence a parallel optical path is characterised by the provision that in a slit lamp or a slit lamp projector an oblique thin glass flat with a partial reflection of the light at a defined angle relative to the optical path is disposed between the lens assemblies of the achromatic doublet lens in the parallel optical path so that one part of the incident rays is incident as deflected light cone onto a detector assembly disposed laterally in the optical path on the housing, which assembly measures the respectively existing luminous intensity, transmits the values so determined to an evaluation and control means which compares the values so received against a predetermined maximum value, calculates the irradiation dose for the phakic or the aphakic eye and, when this value is exceeded, signals this situation on an indicating alarm means known per se and/or reduces the luminous intensity automatically to the predetermined maximum value in a controlled manner.

As the high illumination level is mainly required for small slit widths this solution entails the advantage that the overall brightness on the detector is retained at a low level. When the slit is opened or when the filters are used the illumination (strong dazzling of the patient under examination) is generally reduced so that the overall brightness is hence equally reduced. With a normal slit lamp application the load created by the light is not exceeded.

The present invention will be described in the following by exemplary embodiments, without any restriction of the general inventive idea, with reference to the drawing to which explicit reference is made, by the way, with respect to the disclosure of all the inventive details which are not disclosed more exhaustively in the text.

DESCRIPTION OF EMBODIMENTS

FIG. 1 shows a slit lamp in an embodiment comprising a "slit projector" lens 4. In this model the slit image 1, a reflecting prism 2, the stereo microscope lens 3, the slit projector lens 4, the filter assembly consisting of a colour neutral glass filter 5 and UV absorption filter 6, the slit diaphragm 7, a condenser 8 with IR absorption features, a halogen lamp 9 and a concave mirror 10 are arranged in a manner common for such a configuration. In accordance with the present invention an oblique thin glass flat 11 with a total reflection of 2 percent approximately is disposed in a slit lamp or a slit lamp projector of this kind at an angle of 45 degrees relative to the optical path above the filter assembly consisting of the colour neutral glass filter 5 and the UV absorption filter 6 between the latter and the "slit projector" lens 4. Thus one part of the incident rays is directed as deflected light cone to a detector 12 or a detector assembly, respectively, which is laterally disposed in the housing at a right angle relative to the centre axis of the optical path. The detector 12 or the detector assembly measures the respectively existing luminous intensity, transmits the detected values to an evaluation and control means which is not illustrated in the Figure. The latter means compares the received values against a predetermined maximum value and determines the irradiation dose for the phakic or aphakic eye. When the value is exceeded this situation is signalled to an indicator signalling means and/or the luminous intensity is automatically reduced to the predetermined maximum value in a controlled manner.

Figure 2:
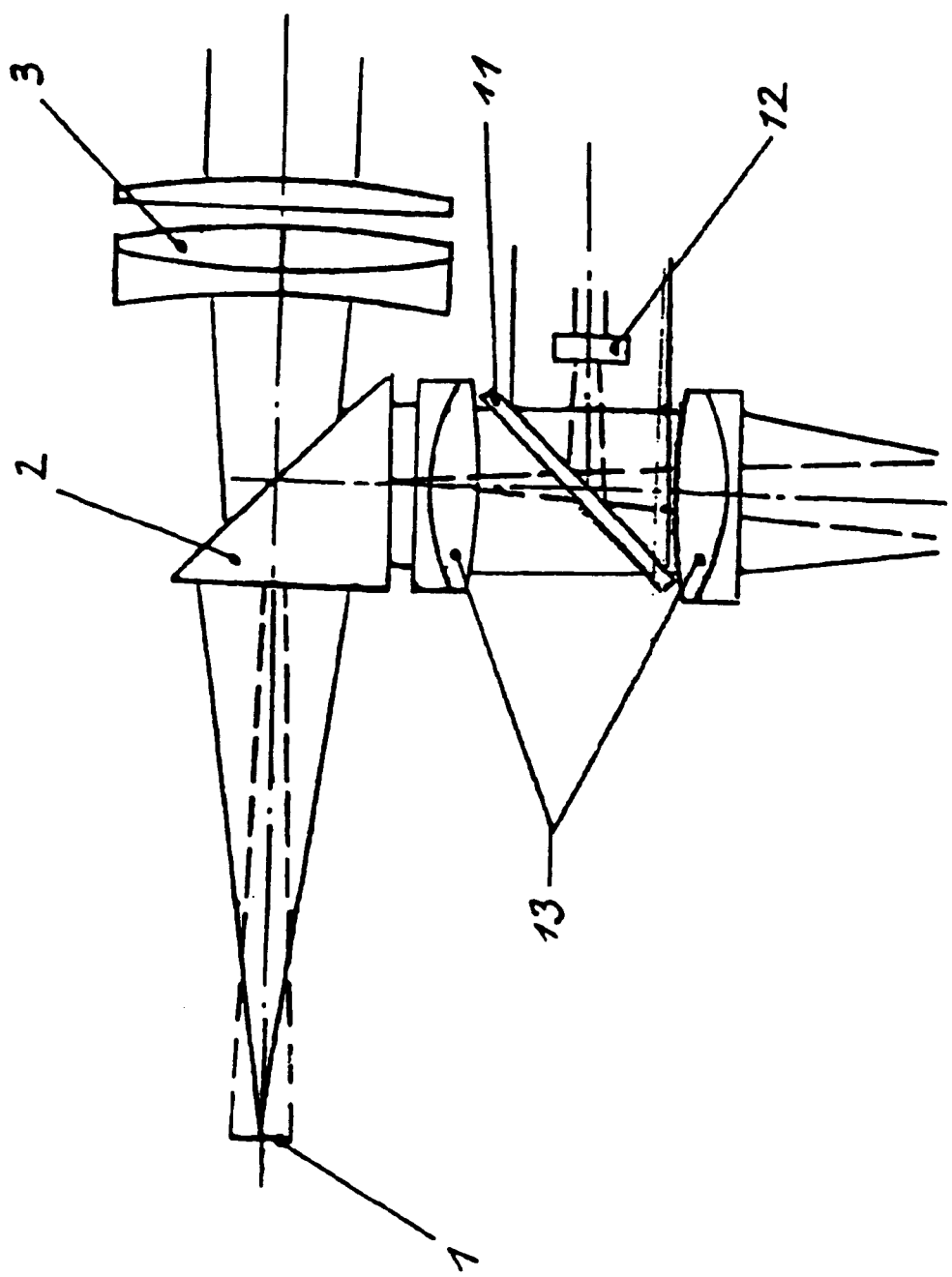

FIG. 2 shows a luminous intensity detection and control system for slit lamps and slit lamp projectors for devices with an achromatic doublet lens (split lenses) and hence a parallel optical path. The slit image 1, the reflecting prism 2, the stereo microscope lens 3 and the components of the achromatic doublet lens 13 are disposed in a manner common for slit lamps or slit lamp microscopes of this configuration. A thin glass flat 11 is arranged in the parallel optical path between the two assemblies of the achromatic doublet lens 13 at an angle of 45 degrees. A detector 12 or a detector assembly, respectively, is again disposed at a right angle relative to the optical path in such a way that one part of the light cone is incident as deflected light cone on the detector.

Figure 3:
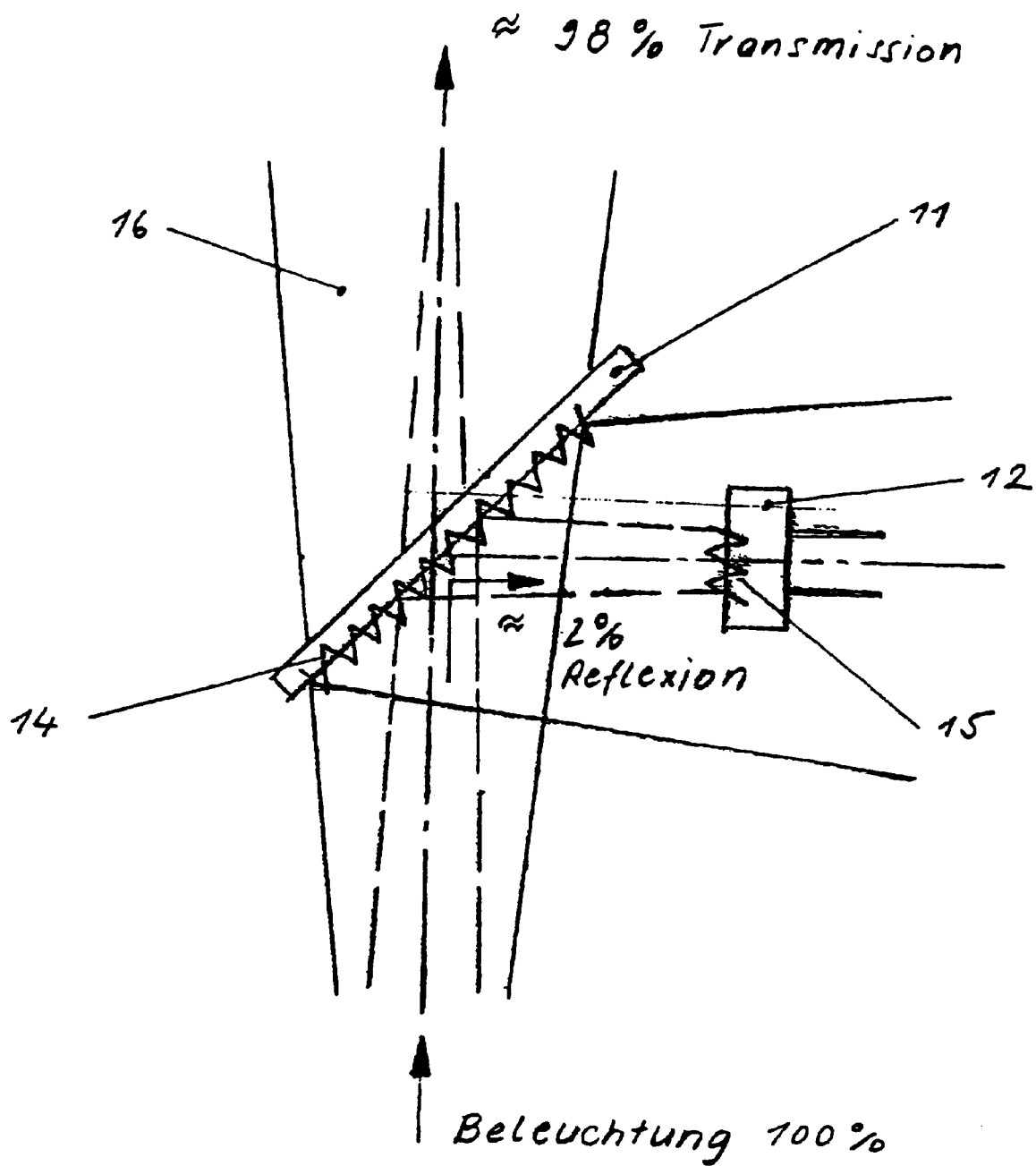

FIG. 3 shows the deflection of one part of the light cone through the thin glass flat 11, the filament image 14 on the thin glass flat 11, and one part of the filament image 15 on the detector 12 as well as the arrangement of the thin glass flat 11 and the detector 12 in the optical illumination path of the slit projector.

What is claimed is:

1. Luminous intensity detection and control system for slit lamps and slit lamp projectors with non-split lenses of the kind of a stereo microscope, characterized in that in a slit lamp or a slit lamp projector an oblique thin glass flat with a partial reflection of the light is disposed at a defined angle relative to the optical path above the filter assembly consisting of a color neutral glass filter and a UV absorption filter between the latter and the "slit projector" lens in such a way that as a result one part of the incident rays is incident as deflected light cone on a detector or a detector assembly, respectively, which is arranged laterally in the housing at an angle relative to the center axis of the optical illumination path in the housing, which detector assembly measures the respectively existing luminous intensity, transmits the detected values to an evaluation and control means which compares the values so received against a predetermined maximum value, calculates the irradiation dose for the phakic or aphakic eye and, when the value is exceeded, signals this situation on an indicating alarm means and/or reduces the luminous intensity automatically to the predetermined maximum value in a controlled manner.

2. Luminous intensity detection and control system for slit lamps and slit lamp projectors for devices including an achromatic doublet lens and hence a parallel optical path, characterized in that in a slit lamp or a slit lamp projector an oblique thin glass flat with a partial reflection of the light is disposed at a defined angle relative to the optical path between the lens assemblies of said achromatic doublet lens in the optical illumination path such that one part of the incident rays is incident as a deflected light cone on a detector or a detector assembly, respectively, which is arranged laterally in the housing at an angle dependent on the angle of said thin glass flat in said housing, which detector assembly measures the respectively existing luminous intensity, transmits the detected values to an evaluation and control means which compares the values so received against a predetermined maximum value, calculates the irradiation dose for the phakic or aphakic eye and, when the value is exceeded, signals this situation on an indicating alarm means and/or reduces the luminous intensity automatically to the predetermined maximum value in a controlled manner.

* * * * *